(12) United States Patent
Littlewood et al.

(10) Patent No.: US 6,503,484 B2
(45) Date of Patent: Jan. 7, 2003

(54) ORAL COMPOSITION

(75) Inventors: David Thomas Littlewood, Bebington (GB); Philip Christopher Waterfield, Bebington (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/923,521

(22) Filed: Aug. 7, 2001

(65) Prior Publication Data

US 2002/0034478 A1 Mar. 21, 2002

(30) Foreign Application Priority Data

Aug. 7, 2000 (EP) .............................. 00306727

(51) Int. Cl.⁷ .............................. A61K 7/16; A61K 7/18
(52) U.S. Cl. .......................................... 424/52; 424/49
(58) Field of Search ...................... 424/49–58

(56) References Cited

U.S. PATENT DOCUMENTS

| | | | | |
|---|---|---|---|---|
| 5,284,648 A | * | 2/1994 | White et al. ................... | 424/49 |
| 5,310,563 A | * | 5/1994 | Curtis et al. ................. | 424/616 |
| 5,372,802 A | * | 12/1994 | Barrows et al. ............... | 424/52 |
| 5,456,902 A | * | 10/1995 | Williams et al. .............. | 424/49 |
| 5,538,667 A | * | 7/1996 | Hill et al. .................... | 252/312 |
| 5,554,358 A | * | 9/1996 | Williams et al. .............. | 422/49 |
| 5,612,307 A | * | 3/1997 | Chambers et al. .......... | 510/446 |
| 5,639,445 A | * | 6/1997 | Curtis et al. .................. | 424/49 |
| 5,645,841 A | * | 7/1997 | Hill et al. .................... | 424/401 |
| 5,651,959 A | * | 7/1997 | Hill et al. ..................... | 424/49 |
| 5,665,374 A | * | 9/1997 | Hill et al. .................... | 424/435 |
| 5,711,936 A | * | 1/1998 | Hill et al. .................... | 424/49 |
| 5,733,529 A | * | 3/1998 | Hill et al. ..................... | 424/49 |
| 5,814,303 A | | 9/1998 | Williams et al. | |

FOREIGN PATENT DOCUMENTS

| | | |
|---|---|---|
| EP | 0 528 457 | 7/1992 |
| GB | 789851 | 3/1956 |
| GB | 2 242 358 | 3/1991 |
| WO | 91/13608 | 9/1991 |
| WO | 94/14405 | 7/1994 |

* cited by examiner

*Primary Examiner*—Shep K. Rose
(74) *Attorney, Agent, or Firm*—Milton L. Honig

(57) ABSTRACT

Oral non-food composition comprising an active agent which is substantially insoluble in water at room temperature and pressure and a silicone with a viscosity within the range $10 \times 10^{-3}$ to $90 \times 10^{-3}$ $m^2 s^{-1}$ at 25° C., said composition obtainable by mixing said active agent and silicone before adding said mixture to the remaining ingredients of the composition.

7 Claims, No Drawings

ORAL COMPOSITION

BACKGROUND OF THE INVENTION

1. Field of the Invention

The present invention relates to an oral non-food composition comprising a high viscosity slow-release material.

2. The Related Art

Modern dental hygiene products typically contain ingredients included to provide a benefit to the consumer. Such ingredients include antimicrobial agents, e.g. Triclosan; anti-caries agents, e.g. fluoride and flavours such as peppermint extract to name but a few.

An obvious problem with including agents in oral preparations is that within a short period of time much of the agent is removed from the oral cavity through the action of rinsing or because of the increased salivation in response to something being put into the oral cavity. The fact that the average consumer brushes approximately once every twelve hours only exacerbates the problem of localising enough agent to have an effect.

There is, therefore, a need for an oral composition which is capable of prolonging the effect of such ingredients.

The prior art includes oral compositions comprising an agent which attempts to prolong the action of such actives. For example U.S. Pat. No. 2,806,814 (Richter) discloses an oral composition comprising a silicone compound and a higher aliphatic acyl amide of an amino carboxylic acid compound. The silicone is stated to act synergistically with the acyl amide to improve the latter antimicrobial and acid inhibiting activity.

EP-B1-0 528 457 (Unilever) describes dentifrice compositions comprising a non-cyclic, hydrophobic amino alkyl silicone in an oil in water emulsion. The silicone is said to form a layer on the teeth and dissolve the antibacterial active. Thus, the active is maintained at the desired location.

EP-B1-0 518 924 (Rolla) discloses a dentifrice composition comprising a silicone oil and a fat-soluble antimicrobial other than hexyl resorcinol. The silicone oil is preferably a diphenyl or di($C_1$–$C_4$) alkyl-polysiloxane which the antimicrobial agent is preferably an antiseptic phenol such as Triclosan (2',4,4'-trichloro,2-hydroxy-diphenyl ether). The silicone is preferably a liquid silicone such as those disclosed in U.S. Pat. No. 2,806,814.

None of the above disclosures describes an oral non-food composition comprising a high viscosity slow-release material such as is required in the invention.

Further examples of disclosures describing the use of silicones in dentifrice compositions include GB 689 679 which discloses a mouthwash comprising an organopolysiloxane. The silicone is included in order to coat the teeth and, thereby, prevent adhesion of food particles, tartar etc. and so reduce staining.

WO 94/14405 (Rydén) discloses dentifrice compositions comprising a dimethyl polysiloxane with a viscosity in the range of 0.4 to $100 \times 10^{-3}$ $m^2s^{-1}$ at 25° C. However, the preferred silicones have a viscosity of 0.2 to $5 \times 10^{-3}$ $m^2s^{-1}$ and the exemplified material, SF-96 (ex. General Electric) has a viscosity towards the bottom end of this preferred range.

Additionally the toothpaste according to this invention requires at least 5% siloxane to achieve the improvement in abrasion.

U.S. Pat. No. 3,507,955 (Osipow) discloses oral compositions comprising 3 to 7% by weight of an anti-caries agent which is a dimethyl siloxane having a viscosity of 0.05 to $5 \times 10^{-3}$ $m^2s^{-1}$, preferably 0.2 to $1 \times 10^{-3}$ $m^2s^{-1}$.

WO 95/15740 (3M) discloses a coating for teeth to reduce or prevent adhesion of bacteria and proteinaceous material. These coatings comprise a hydrophobic graft polysiloxane chain having a molecular weight of at least 500.

EP-B1-0 373 688 (Unilever) discloses dentifrices comprises an amino alkyl silicone. While silicones with a molecular weight of 10000 to 30000 are preferred, however, providing that the silicone spreads over the teeth enamel by brushing and rinsing there is no maximum or minimum molecular weight.

EP-B1-0 371 551 (Unilever) discloses a dentifrice composition comprising an amino alkyl silicone which has a molecular weight between 5000 and 100000 it is also noted that a viscosity in the range of 0.05 to $3 \times 10^{-3}$ $m^2s^{-1}$ (page 5, line 9) is required.

EP-B1-0 528 457 (Unilever) discloses dentifrice compositions comprising an amino alkyl siloxane. The siloxane preferably has a molecular weight ranging from 5000 to 100000 which those silicones with a molecular weight as high as 1000000 or more may also be used. However, the preferred viscosity for the amino alkyl siloxane ranges from 0.05 to $3 \times 10^{-3}$ $m^2s^{-1}$ (page 5, line 51).

GB 1 194 885 (Pre-Coat Corp) discloses dentifrices comprising silicone oils which will preferentially coat teeth. The dimethyl polysiloxanes usually have a viscosity of 0.04 to $100 \times 10^{-3}$ $m^2s^{-1}$ at 25° C. and the preferred siloxanes have a viscosity in the range 0.2 to $5 \times 10^{-3}$ $m^2s^{-1}$. The exemplified silicone SF-96 has a viscosity ranging from 0.5 to $10 \times 10^{-3}$ $m^2s^{-1}$.

Thus, it is a primary object of the invention to provide an oral, non-food composition which comprises a high viscosity, slow-release material which prolongs the effect of therapeutic, sensory or other active agents contained therein.

SUMMARY OF THE INVENTION

Accordingly, the invention provides an oral, non-food composition which includes an active agent that is substantially insoluble in water at room temperature and pressure and a silicone with a viscosity within the range $10 \times 10^{-3}$ to $90 \times 10^{-3}$ $m^2s^{-1}$ at 25° C., characterised in that the composition comprises an intimate blend of the active and silicone.

An essential feature of the invention is the silicone which effects a slow release of beneficial active agents additionally present in the composition. Such a silicone is thus capable of prolonging the effect of such beneficial active agents in the oral cavity. In order to provide such an intimate blend of active and silicone it is preferred that the two are admixed before blending with the remaining ingredients of the composition.

Silicones according to the present invention may include any of the organopolysiloxanes known in the art which have a viscosity ranging from $10 \times 10^{-3}$ to $90 \times 10^{-3}$ $m^2s^{-1}$. Examples of such silicones include dimethyl siloxanes, e.g. the 200 series available commercially from Dow Corning.

Preferably, the slow-release material of the invention is a silicone having a viscosity ranging from $10 \times 10^{-3}$ to $90 \times 10^{-3}$ $m^2s^{-1}$, more preferably from $30 \times 10^{-3}$ to $90 \times 10^{-3}$ $m^2s^{-1}$ and especially between $50 \times 10^{-3}$ and $70 \times 10^{-3}$ $m^2s^{-1}$.

DETAILED DESCRIPTION OF THE INVENTION

An object of the invention is the prolonging of an effect of an active agent. Such an active agent may have any of a number of effects, e.g. therapeutic, sensory or cosmetic. It may even have a combination of any of these or other effects.

In a preferred embodiment of the invention the active agent is one which is substantially insoluble in water. By substantially insoluble means that the agent may be sparingly soluble. Such agents include tin pyrophosphate, zinc citrate, magnesium fluoride and calcium fluoride to name a few. Such actives are typically present at amounts ranging from 0.01 to 10% by weight, preferably from 0.5 to 5% by weight.

The silicone of the present invention is particularly suitable in so-called 'double-pump products' where two formulations are stored in separate containers and mixed immediately prior to use. Typical of such double-pump products is that marketed by Unilever under the brand name Mentadent® in the US where a gel formulation comprising hydrogen peroxide and a paste formulation comprising sodium bicarbonate are stored separately and mixed immediately prior to use to allow the creation of oxygen bubbles in the oral cavity.

A problem with using silicones in dentifrice formulations is that the silicone acts as an anti-foam agent and the anti-foam effect is proportional to the length of chains in the silicone: the longer the silicone chain the greater the effect. For this reason long-chain silicones have not been readily used as ingredients in dentifrice formulations.

However, we have surprisingly found that a silicone according to the invention can be successfully incorporated into the peroxide gel formulation of a double-pump product, additionally comprising a bicarbonate paste formulation, and not significantly reduce the foaming of the dentifrice when the two formulations are combined.

A composition according to the invention will comprise from 0.001 to 10% by weight of the silicone, preferably from 0.1 to 3% and especially from 0.2 to 2%.

The composition according to the invention may be any oral, non-food composition, e.g. toothpaste and may be in the form of a gel, paste, gum or any other suitable type.

In a further aspect to the invention there is provided the use of a silicone having a viscosity ranging from $10 \times 10^{-3}$ to $90 \times 10^{-3}$ $m^2s^{-1}$ at 25° C. in an oral composition as a slow-release material for an active agent.

All viscosities in this application are at 25° C. unless otherwise stated and can be measured on a Brookfield Viscometer according to standard protocols.

The composition according to the invention may also comprise ingredients which are common in dentifrices. Examples of such ingredients include:

antimicrobial agents, e.g. Triclosan, chlorhexidine, copper-, zinc- and stannous salts such as zinc citrate, zinc sulphate, zinc glycinate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);

anti-inflammatory agents such as ibuprofen, flurbiprofen, aspirin, indomethacin etc.;

anti-caries agents such as sodium or stannous fluoride, aminefluorides, disodium monofluorophosphate, sodium trimeta phosphate and casein;

plaque buffers such as urea, calcium lactate, calcium glycerophosphate and strontium polyacrylates;

vitamins such as Vitamin C;

plant extracts;

desensitising agents, e.g. potassium citrate, potassium chloride, potassium tartrate, potassium bicarbonate, potassium oxalate, potassium nitrate and strontium salts;

anti-calculus agents, e.g. alkali-metal pyrophosphates, hypophosphite-containing polymers, organic phosphonates and phosphocitrates etc.;

gum protection agents, e.g. vegetable oils such as sunflower oil, rape seed oil, soybean oil and safflower oil; silicone oil; and hydrocarbon oil. The gum protection agent may be an agent capable of improving the permeability barrier of the gums. A complete description of agents capable of improving the permeability barrier of the gum is found in our co-pending application GB;

biomolecules, e.g. bacteriocins, antibodies, enzymes, etc.;

flavours, e.g. peppermint and spearmint oils;

preservatives;

opacifying agents;

colouring agents;

pH-adjusting agents;

sweetening agents;

pharmaceutically acceptable carriers, e.g. starch, sucrose, water or water/alcohol systems etc.;

surfactants, such as anionic, nonionic, cationic and zwitterionic or amphoteric surfactants;

particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials;

humectants such as glycerol, sorbitol, propyleneglycol, xylitol, lactitol etc.;

binders and thickeners such as sodium carboxymethylcellulose, xanthan gum, gum arabic etc. as well as synthetic polymers such as polyacrylates and carboxyvinyl polymers such as Carbopol®;

buffers and salts; and other optional ingredients that may be included are e.g. bleaching agents such as peroxy compounds e.g. potassium peroxydiphosphate, effervescing systems such as sodium bicarbonate/citric acid systems, colour change systems, and so on.

The invention will now be illustrated by way of the following non-limiting examples:

EXAMPLE 1

The following are typical formulations for the gel and paste component parts of a dual-stream product. The gel component comprises polydimethyl siloxane (DC 200 series $60 \times 10^{-3}$ $m^2s^{-1}$ ex. Dow Corning) as slow-release material according to the invention. The paste formulation can be made by any process common in the art. The gel formulation is made by making a base formulation comprising all ingredients save the silicone and the active, which were mixed together beforehand and added to the base formulation afterwards.

Gel component

| Chemical Name | Trade Name | Supplier | 0.25% PDMS | 0.5% PDMS | 0.75% PDMS | 1.0% PDMS |
|---|---|---|---|---|---|---|
| Active (zinc citrate) | | | active at 4% | active at 4% | active at 4% | active at 4% |
| Glycerol | Pricerine 9083 | Unichema | 30.00 | 30.00 | 30.00 | 30.00 |
| Sorbitol | Neosorb | Roquette | 10.00 | 10.00 | 10.00 | 10.00 |
| EO-PO-EO block copolymer | Pluronic F127 | BASF | 20.00 | 20.00 | 20.00 | 20.00 |
| Polyethylene Glycol | PEG 1500 | Breox | 1.00 | 1.00 | 1.00 | 1.00 |
| Hydrogen peroxide | Hydrogen peroxide FMC (35%) | FMC Corp | 4.285 | 4.285 | 4.285 | 4.285 |
| Orthophosphoric acid (85%) | Phosphoric acid | JT Baker | 0.150 | 0.150 | 0.150 | 0.150 |
| Blue Dye | Colour 1206 FD&C Blue #1 | DF Anstead | 0.005 | 0.005 | 0.005 | 0.005 |
| Polydimethylsiloxane | Dow Corning 200 Fluid $60 \times 10^{-3} m^2 s^{-1}$ | Dow Corning | 0.25 | 0.5 | 0.75 | 1.0 |
| Deionised water | — | Local | to 100% | to 100% | to 100% | to 100% |
| TOTAL | | | 100.00 | 100.00 | 100.00 | 100.00 |

Paste component

| Chemical Name | Trade Name | Supplier | % w/w |
|---|---|---|---|
| 70% Sorbitol (N/C) | Neosorb 70/120 | Roquette | 46.16 |
| Deionised Water | Water | Local | 8.40 |
| Polyethylene Glycol | PEG 1500 | Breox | 5.20 |
| Sodium Saccharin | Saccharin | Boots | 0.25 |
| Sodium Fluoride | Sodium Fluoride | Solvay | 0.44 |
| Titanium Dioxide | Titanium Dioxide | Whitaker, Clark & Daniels, Inc | 0.50 |
| Silica | AC 77 | Crosfields | 15.00 |
| Silica | TC-15 | Crosfields | 6.00 |
| Sodium carboxymethyl cellulose | SCMC 9m31xf-U | Aqualon | 0.95 |
| Sodium Bicarbonate | Sodium Bicarbonate | Brunner Mond | 10.00 |
| Sodium lauryl sulphate | Stepanol WA 100 NE/USP | Stepan | 3.20 |
| Ethanol | Ethanol 99% | Hayman | 2.50 |
| Flavour | | | 1.10 |
| Menthol | Menthol Crystals USP | Irving R Boody & Co. Inc | 0.30 |
| TOTAL | | | 100.00 |

EXAMPLE 2

The following constitutes an example of a single-phase formulation comprising a slow-release material according to the invention. The formulation may be made by mixing the zinc citrate and the silicone before adding to a mixture of the remaining ingredients.

| Trade Name | Supplier | % w/w |
|---|---|---|
| NEOSORB 70/70 | ROQUETTE | 45.000 |
| SORBOSIL TC15 | CROSFIELD | 8.000 |
| FLAVOUR | | 1.200 |
| SCMC 9M31XF-U | AQUALON | 0.900 |
| ZINC CITRATE | HAARMANN & REIMER | 0.750 |
| IRGACARE MP | CIBA GEIGY | 0.300 |
| TIONA AG | SCM CHEMICALS | 0.500 |
| SODIUM SACCHARIN | BOOTS | 0.200 |
| EMPICOL 0045 | ALBRIGHT & WILSON | 1.500 |
| SMFP | ALBRIGHT & WILSON | 0.800 |
| DOW CORNING 200 FLUID $60 \times 10^{-3} m^2 s^{-1}$ | DOW CORNING | 1.000 |
| WATER | PPM SECTION | 27.850 |
| BEROX PEG 1500 PHARMACEUTICAL | HONEYWILL & STEIN | 2.000 |
| SORBOSIL AC77 | CROSFIELD | 10.000 |
| TOTAL | | 100.000 |

EXAMPLE 3

The slow-release effect can be demonstrated by the following protocol which shows how the presence of the slow-release material increases the antimicrobial efficacy of a typical antimicrobial agent in a toothpaste formulation.

The principal involves the analysis of the growth of a pure biofilm of bacteria, formed in the wells of a 96-well microtitre plate. The bacteria are treated with toothpaste slurries and the time taken to reach a chosen turbidity is recorded.

One hundred and fifty ml Brain Heart Infusion (BHI) medium (ex. Oxoid) was innoculated with 1 ml bacterial innoculum (*Enterobacter cloacae*) and incubated at 37° C. overnight. Ninety ml of this overnight culture was centrifuged at 3500 rpm for 5 mins and the supernatant decanted. The pellet was resuspended in 5 ml Phosphate Buffered Saline (PBS) and the centrifugation and resuspension steps were repeated twice.

The final suspension was diluted in PBS to achieve an optical density of 0.2 (+/−0.01) with a microtitre plate reader fitted with a 630 nm filter.

One hundred and ninety microlitres of the bacterial suspension was pipetted into each of 96 wells on the microtitre plate and the plate left for 24 h at room temperature. The suspensions were then tipped out of the wells and the plate patted dry on a paper tissue.

Two hundred microlitres sterile 20% glycerol solution was pipetted into each well of the microtitre plate.

Ninety microlitres of the overnight culture was enough to prepare 20 plates which could be stored at this stage in the freezer at −80° C. until required.

Prior to use the plates were defrosted for 30–60 min and the wells were emptied and the plate dried on a paper tissue according to standard procedures.

Enough toothpaste slurry was prepared by weighing out paste and diluting 1:4 with water. The mixture was agitated thoroughly for 30 min and centrifuged for 30 min at 3500 rpm. The supernatant was collected and retained.

Two hundred microlitres of the test slurry was transferred to the biofilm plate and exposed for 30 s before being removed and patted dry in the usual manner. The wells were washed in PBS and dried three times before 200 µl BHI and 80 µl sterile mineral oil was pipetted into each.

The plate was then analysed using a microtitre plate reader. The microtitre plate reader of choice, Dynatech Dial Microtitre Plate Spectrophotometer 2B1037, has a kinetic program which determines the mean times for wells to reach a certain optical density, usually 0.5.

A typical test toothpaste gel slurry (as in example 1) comprising 4% zinc citrate (ZCT) and 0.8% polydimethyl siloxane (PDMS) (Dow Corning 200 series $60 \times 10^{-3}$ $m^2s^{-1}$) was analysed and compared to an identical sample without the siloxane and a control slurry comprising no ZCT.

Four replicates of each of the three samples was analysed in eight parallel rows of wells on the microtitre plate. The amount of time (h) to reach the chosen turbidity (0.5), i.e. the amount of time required for regrowth, was averaged for each of eight rows for each replicate and are presented in Table 1.

It is clear from the results of bacterial regrowth analysis that the presence of the high viscosity slow-release agent increases the efficacy of the antimicrobial agent.

TABLE 1

| Number | Replicate | Mean for 8 samples Time to reach OD = 0.5 (Hours) |
| --- | --- | --- |
| 1 | Gel | 4.978 |
| 2 | Gel | 4.817 |
| 3 | Gel | 5.289 |
| 4 | Gel | 5.085 |
| 5 | Gel + ZCT + PDMS | 7.870 |
| 6 | Gel + ZCT + PDMS | 7.806 |
| 7 | Gel + ZCT + PDMS | 7.829 |
| 8 | Gel + ZCT + PDMS | 7.917 |
| 9 | Gel + ZCT | 6.724 |
| 10 | Gel + ZCT | 6.708 |
| 11 | Gel + ZCT | 6.819 |
| 12 | Gel + ZCT | 6.974 |

What is claimed is:

1. Oral non-food composition comprising:
   (i) from 0.01 to 10% by weight of an active agent which is substantially insoluble in water at room temperature and pressure;
   (ii) from 0.001 to 10% by weight of a silicone with a viscosity within the range $10 \times 10^{-3}$ to $90 \times 10^{-3}$ $m^2s^{-1}$ at 25° C.; and
   (iii) a dental agent selected from the group consisting of an anti-caries agent, a desensitizing agent which is potassium nitrate or a strontium salt, a flavor, a sweetening agent and combinations thereof, each in an effective amount to provide their stated function;
wherein said active and silicone are intimately pre-blended together before addition to other components of said composition.

2. Oral composition according to claim 1, characterised in that the silicone has a viscosity ranging from $30 \times 10^{-3}$ to $90 \times 10^{-3}$ $m^2s^{-1}$.

3. Oral composition according to claim 1, characterised in that the active agent is selected from the group consisting of zinc citrate, magnesium fluoride and calcium fluoride.

4. Oral composition according to claim 1, characterised in that the silicone is an organopolysiloxane.

5. Oral composition according to claim 1, characterised in that the silicone comprises 0.1 to 3% by weight.

6. Oral non-food composition comprising:
   (i) from 0.01 to 10% by weight of zinc citrate as an active agent which is substantially insoluble in water at room temperature and pressure;
   (ii) from 0.001 to 10% by weight of a silicone with a viscosity within the range $10 \times 10^{-3}$ to $90 \times 10^{-3}$ $m^2s^{-1}$ at 25° C.; and
   (iii) a dental agent selected from the group consisting of an anti-caries agent, a desensitizing agent which is potassium nitrate or a strontium salt, a flavor, a sweetening agent and combinations thereof, each in an effective amount to provide their stated function;
wherein said active and silicone are present as an intimate blend.

7. A dentifrice comprising two formulations which are stored separately and mixed immediately prior to use, a first of the two formulations comprising a peroxide suspended within a gel, a second of the two formulations comprising a bicarbonate suspended within a paste, and wherein at least one of the gel or paste formulations comprises:
   (i) from 0.01 to 10% by weight of an active agent which is substantially insoluble in water at room temperature and pressure;
   (ii) from 0.001 to 10% by weight of a silicone with a viscosity within the range $10 \times 10^{-3}$ to $90 \times 10^{-3}$ $m^2s^{-1}$ at 25° C.; and
   (iii) a dental agent selected from the group consisting of an anti-caries agent, a desensitizing agent which is potassium nitrate or a strontium salt, a flavor, a sweetening agent and combinations thereof, each in an effective amount to provide their stated function;
wherein said active and silicone are intimately pre-blended together before addition to other components of said composition.

* * * * *